United States Patent [19]

Kim et al.

[11] Patent Number: 4,495,193

[45] Date of Patent: Jan. 22, 1985

[54] IMIDAZOLE COMPOUNDS WHICH REDUCE GASTRIC ACID SECRETION

[75] Inventors: Sun H. Kim, Chestnut Hill; Jacques-Pierre Moreau, Upton, both of Mass.

[73] Assignee: Biomeasure, Inc., Hopkinton, Mass.

[21] Appl. No.: 454,733

[22] Filed: Dec. 30, 1982

[51] Int. Cl.³ .................. A61K 31/415; C07D 403/12
[52] U.S. Cl. .................... 514/385; 544/144;
544/373; 546/200; 548/253; 548/336; 548/465;
548/472; 514/381; 514/382
[58] Field of Search ............... 548/336, 253;
424/273 R, 269

[56] References Cited

U.S. PATENT DOCUMENTS 3,987,174 10/1976 Cotrel et al. ............... 546/200 X
4,128,658 12/1978 Price et al. ............... 424/285

FOREIGN PATENT DOCUMENTS 875846 10/1979 Belgium ............... 548/267
1397436 6/1975 United Kingdom ............... 548/342

OTHER PUBLICATIONS

Lumma, W., et al., *J. Med. Chem.* 25, 207–210 (1982).
Algieri, A., et al., J. Med. Chem. 25, 210–212 (1982).

*Primary Examiner*—Richard A. Schwartz

[57] ABSTRACT

A compound having gastric acid secretion reducing activity and having the formula

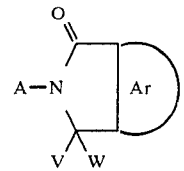

wherein each V and W, independently, is H, $-CH_2COOR^4$ where $R^4$ is H or lower alkyl, $-CH_2CN$, or

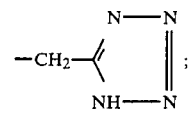

or V and W together represent $=CHCOOR^4$ or $=CHCN$; A is

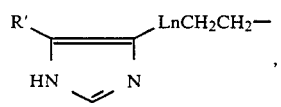

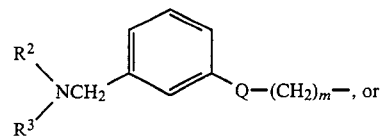

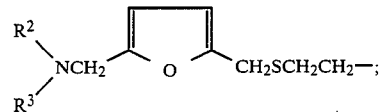

$R^1$ is H or $CH_3$; L is $CH_2S$; Q is O or $CH_2S$; n is 0 or 1; 2 m 4; each $R^2$ and $R^3$, independently, is hydrogen, lower alkyl, lower cycloalkyl, or lower aralkyl; or $R^2$ and $R^3$, together with the nitrogen atom to which they are attached, form a 4, 5, or 6 membered heterocyclic ring containing 0, 1, or 2 oxygen atoms and 1, 2, or 3 nitrogen atoms and being unsubstituted or lower alkyl substituted; and Ar is a single ring aromatic group selected from aryl, substituted aryl, fused aryl, or heteroaryl; or the pharmaceutically acceptable salt thereof.

7 Claims, No Drawings

IMIDAZOLE COMPOUNDS WHICH REDUCE GASTRIC ACID SECRETION

BACKGROUND OF THE INVENTION

This invention relates to compounds that block gastric secretion.

Such compounds, which may be histamine $H_2$ receptor antagonists, reduce the volume and acidity of gastric secretions caused by a variety of stimuli, e.g., insulin, histamine, gastrin, food, and parasympathetic activity.

SUMMARY OF THE INVENTION

In general, the invention features compounds having gastric secretion reducing activity and having the formula

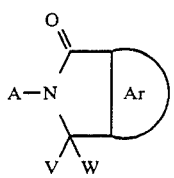
(1)

wherein each V and W, independently, is H, —$CH_2CN$,

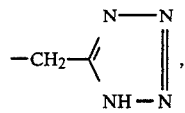

or —$CH_2COOR^4$ where $R^4$ is H or lower (fewer than 6 carbon atoms) alkyl; or V and W together represent =$CHCOOR^4$ or =CHCN; and A is chosen from

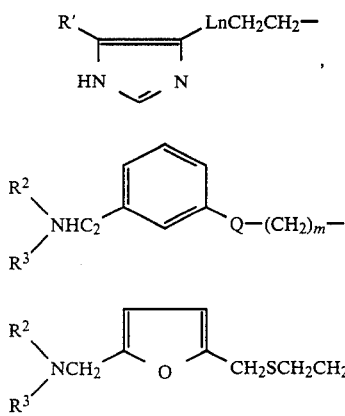

wherein $R^1$ is H or $CH_3$; L is $CH_2S$; Q is O or $CH_2S$; n is 0 or 1; $2 \leq m \leq 4$; each $R^2$ and $R^3$, independently, is hydrogen, lower alkyl, lower cycloalkyl, or lower aralkyl, or $R^2$ and $R^3$, together with the nitrogen atom to which they are attached, form a 4, 5, or 6 membered heterocyclic ring containing 0, 1, of 2 oxygen atoms and 1, 2, or 3 nitrogen atoms and being unsubstituted or lower alkyl substituted; and Ar is a single-ring aromatic group selected from the aryl, substituted aryl, fused aryl, or heteroaryl groups; or a pharmaceutically acceptable salt thereof.

In preferred embodiments, the compound is N-(4-imidazolylethyl)-1-isoindolidone; N-(4-imidazolylethyl)-3-ethoxycarbonylmethylene-isoindolidone; 4-(N-(1'-isoindolidonyl)-2-ethylthiomethyl)-5-methylimidazole; 2-(4-(3-(1-piperidinylmethyl)-phenoxy) butyl)-1H-isoindole-1one; or 2-(3-(3-(1-piperidinylmethyl)phenoxy)propyl-1H-isoindole-1-one.

The compounds are potent, non-mutagenic, stable, and will pass through the stomach without losing their effectiveness. Furthermore, manufacture is relatively simple and inexpensive.

Other features and advantages of the invention will be apparent from the following description of the preferred embodiments, and from the claims.

DESCRIPTION OF THE PREFERRED EMBODIMENTS

We turn now to a description of preferred embodiments of the invention.

Structure

The compounds have the general formulae (1), (2), (3), and (4). Examples of preferred compounds within those formulae are those referred to as preferred embodiments above.

Compounds of the invention are N-substituted lactam derivatives fused to an aryl or heteroaryl ring. The N-substitution is characterized by a straight chain of two to four carbon atoms which can also contain a sulfur or oxygen bridge. This straight chain terminates in an aryl or heteroaryl ring which can be substituted or unsubstituted. All the compounds can exhibit tautomerism, and the formulae are intended to cover all tautomers.

The compounds or pharmaceutically acceptable salts thereof can be administered alone or in combination with a pharmaceutically acceptable carrier or diluent.

Acceptable salts include hydrochlorides, hydrobromides, and sulfates. Particularly useful organic acid salts are acetates, maleates, and fumarates.

For oral administration the pharmaceutical composition can most conveniently be in the form of capsules or tablets, which can be slow release tablets. The composition can also be in the form of a dragee or syrup.

Synthesis

The above compounds can be synthesized as follows. A primary amine of Formula (5), (6), or (7)

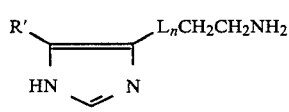
(5)

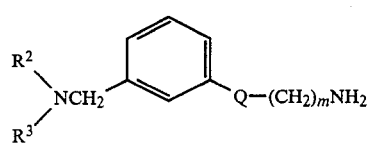
(6)

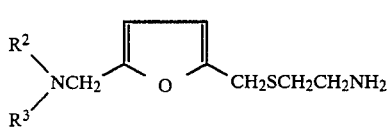
(7)

is reacted with the appropriate anhydride, e.g.,

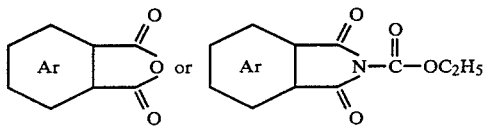

in either a protic or aprotic solvent to form one of the following intermediates:

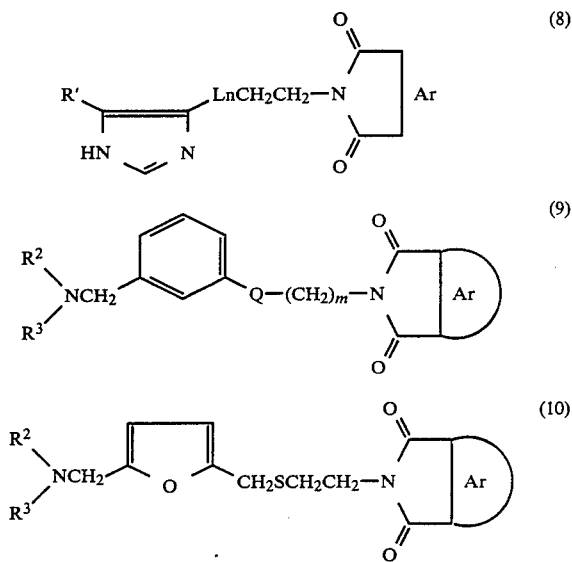

Certain compounds of formula (9), those in which Ar is benzene, are prepared more conveniently by an alternative method than from a precursor of formula (6). This alternative method is described in the literature, i.e., Bel. Patent No. 875,846 (1979).

These intermediate compounds (Formulae (8), (9), or (10)) can be selectively reduced by diobrane (Yoon et al. (1973) J. Org. Chem. 38, 2786; Brown et al. (1973) J. Org. Chem. 38, 912; Kornet et al. (1968) J. Org. Chem. 33, 3637) or by acid catalyzed hydrogenation (McAlees et al (1977) J. Chem. Soc., Perkin I, 2038) to produce the N-substituted isoindoline-1-ones below:

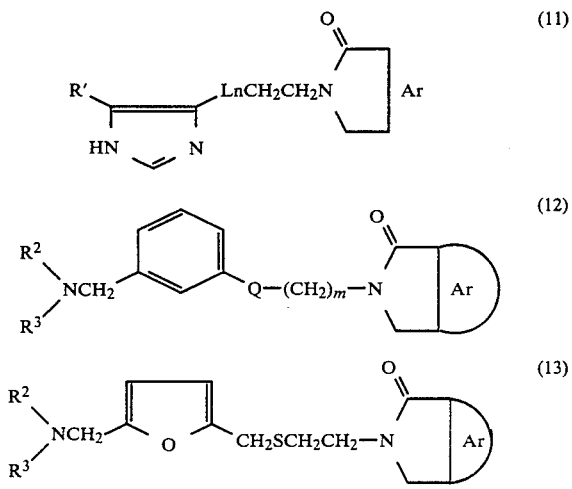

Diborane reduction can be carried out in tetrahydrofuran, and catalytic hydrogenation in ethylacetate/trifluoroacetic acid. These reduction reactions should be carried out under an inert atmosphere, such as nitrogen, argon, or hydrogen.

Intermediates (8), (9), and (10) are alkenylated under an inert atmosphere using conventional Wittig or Witting-Horner reagents, e.g., $(C_6H_5)_3P=CHR^4$ where $R^4$ is H, $COOC_2H_5$, or CHCN; or $(R^6)_2$

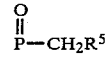

where $R^5$ is $COOR^7$ or CN and each $R^6$ and each $R^7$ is lower alkyl. Alkenylation can be carried out neat or in an inert organic solvent such as benzene or xylene. Alkenylation is discussed in Flitsh & Schindle (1975) Synthesis, pp. 678-700.

Specific compounds are made as follows.

N-(4-imidazolylethyl)-1-isoindolidone 3 ml of triethylamine are added to a suspension of 3.7 gm of histamine dihydrochloride in 50 ml of dry THF. Following the stepwise addition of 4 gm N-carboethoxyphthalimide, the mixture is stirred at room temperature overnight. The product of this reaction, N-phthaloylhistamine, is retrieved from the reaction mixture, dissolved in ethylacetate, washed with water several times, and dried over $MgSO_4$. The crude N-phthaloylhistamine is then recrystallized from ethylacetate to yield 4 gm of purified product. N-phthaloylhistamine is also prepared by using aqueous $Na_2CO_3$ instead of organic solvents.

300 mg of purified N-phthaloyl histamine are dissolved in 10 ml of a 1:4 mixture of trifluoroacetic acid and ethylacetate. 300 mg of 10% palladium-charcoal are added to the mixture as a catalyst, and the N-phthaloyl histamine is hydrogenated under one atmosphere of hydrogen for 48 hrs.

Following filtration through a celite pad, the residue is treated with water and aqueous sodium carbonate. The N-(4-imidazolylethyl)-1-isoindolidone is extracted from the aqueous solution with chloroform. The organic layer is then washed with water and dried over $MgSO_4$. After evaporation of the solvent the synthetic product is purified by silical gel chromatography using a 9:1 mixture of $CHCl_3$ and $CH_3OH$ as the eluant. Appropriate fractions (TLC: $CHCL_3/MeOH=3:1$ Rf=0.46. Starting material Rf=0.57) are pooled, and the solvent is removed in vacuo to dryness. 160 mg of a colorless solid are obtained, m.p. 168°–170° C., Mass: 227 (calculated 227).

N-(4-imidazolylethyl)-1-isoindolidone is also obtained using diborane reduction.

N-(4-imidazolylethyl)-3-carbethoxymethyleneisoindoline

A mixture of 240 mg of N-phthaloylhistamine (prepared as described above) and 700 mg of carbethoxymethylene-triphenylphosphorane in 6 ml of xylene is refluxed overnight. The solvent is removed in vacuo, and the residue is purified by silica gel chromatography using chloroform as the eluant.

Appropriate fractions (TLC: $CHCl_3/MeOH=4:1$, Rf=0.41) are pooled, and the solvent is removed in vacuo to provide 85 mg of a pale yellow solid. Mass: 311 (calculated value: 311).

Similar results are also obtained by the fusion method, setting the reaction mixture in a bath at 140°–150° C. for 5–8 hours under a nitrogen atmosphere.

4-(N-(1'-isoindolidonyl)-2-aminoethylthiomethyl)-5-methylimidazole 75 mg. of sodium borohydride are added to a solution of 200 mg 4-(n-phthaloyl-2-aminoethylthiomethyl)-5-methylimidazole in 10 ml dry tetrahydrofuran. The mixture is then cooled in an ice bath, and 0.33 ml boron trifluoride etherate is added dropwise under a nitrogen atmosphere. After being stirred at room temperature for 1 hr, the mixture is refluxed for 2 hrs. Following the careful addition of 2.5 ml of 30% ethanolic HCl, the mixture is refluxed for an additional ½ hr. The solvents are removed in vacuo, and the residue dissolved in water, treated with sodium carbonate, and then extracted from the aqueous solution with chloroform. The organic layer is then washed with water and dried over MgSO4. After evaporation of solvent the residue is chromatograhed on preparative silica gel using CHCl3 and MeOH in a 9:1 ratio as a developing solvent. Appropriate fractions (TLC: CHCl3/MeOH (3:1) Rf=0.3, starting material Rf=0.41) are pooled, and the solvent removed in vacuo to provide 100 mg of a pale yellow foam.

2-(4-(3-(1-piperidinylmethyl)phenoxy)butyl)-1H-isoindole-1-one 340 mg of 2-(4-(3-(1-piperidinylmethyl)phenoxy)butyl-1H-isoindole-1, 3(2H)-dione are dissolved in 30 ml of 1:1 mixture of ethylacetate and trifluoroacetic acid. 340 mg of 10% palladium-charcoal catalyst are added to the solution, which is then hydrogenated under 30 p.s.i. of hydrogen for 48 hours. The crude product is recovered by filtration through a celite pad, and the solvent is evaporated. The product is then suspended in water, treated with 2 N-NaOH, extracted from the aqueous solution with two washings of ethylacetate, and dried over MgSO4. Upon evaporation of the solvent, 288 mg of purified product are recovered. TLC (Silica gel, CHCl3-MeOH=9:1) Rf=0.36. IR (CHCl3) 1680 cm$^{-1}$(—COM—). Mol: 378 (Molecular ion).

In an analagous manner 2-(3-(3-(1-piperidinylmethyl)phenoxy)propyl)-1H-isoindole1-one is obtained from (2-(3-(3-(1-piperidinylmethyl)phenoxy)propyl)-1H-isoindole-1, 3(2H) dione. IR (CHCl3). 1080 cm$^{-1}$(—COM—). TLC (Silica gel, CHCl3—MeOh=9:1) Rf=0.26.

Use

When administered to mammals (e.g. orally, topically, intravenously, parenterally, nasally, or by suppository), the compounds of the invention can reduce gastric acid secretion.

This action can render the compounds useful in the treatment of peptic, gastric, or duodenal ulcers, Zollinger-Ellison syndrome (gastrinoma), systemic mastocytosis, basophil leukemia associated with hyperhistamenia, short bowel syndrome, reflux esophagitis, acute erosive gastritis, and pancreatic insufficiency.

The compounds can be administered to a mammal in a dosage of 2 to 10 mg/kg/day, preferably 4 to 8 mg/kg/day.

We claim:

1. A compound having gastric acid secretion reducing activity and having the formula

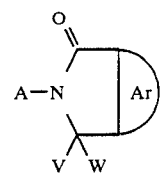

wherein each V and W, independently, is H, —CH2CN,

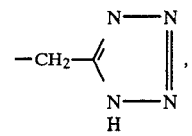

or —CH2COOR$^4$ where R$^4$ is H or a lower alkyl; or V and W together represent =CHCOOR$^4$ or =CHCN; A is

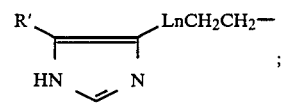

and Ar is benzene; or the pharmaceutically acceptable salt thereof.

2. The compound of claim 1, wherein A is

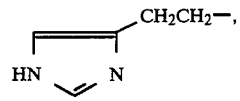

V is H, W is H, and Ar is benzene; said compound having the name N-(4-imidazolylethyl)-1-isoindolidone; or the pharamaceutically acceptable salt thereof.

3. The compound of claim 1, wherein A is

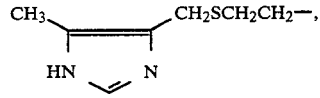

V is H, W is H, and Ar is benzene; said compound having the name 4-(N-(1'-isoindolidonyl)-2-ethylthiomethyl)-5-methylimidazole; or the pharmaceutically acceptable salt thereof.

4. The compound of claim 1, wherein A is

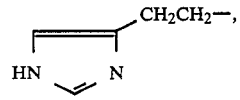

Ar is benzene, and V and W together represent

said compound having the name N-(4-imidozolylethyl)-3-ethoxycarbonylmethylene-isoindolidone; or the pharmaceutically acceptable salt thereof.

5. A therapeutic composition for treating gastric hypersecretion comprising a therapeutically effective amount of the compound of claim 1 together with a pharmaceutically acceptable carrier substance.

6. The therapeutic composition of claim 5, wherein said composition is in the form of a tablet, capsule, or liquid for oral administration to a human patient in need of said compound.

7. A method of treating a mammal suffering from gastric hypersecretion comprising administering to said mammal a gastric secretion reducing amount of the compound of claim 1, 2, 3, or 4.

* * * * *